United States Patent [19]

Yates

[11] 4,332,654
[45] Jun. 1, 1982

[54] PHOTOACTIVATED CATALYTIC HYDROSILYLATION OF CARBONYL COMPOUNDS

[75] Inventor: Ronald L. Yates, Midland, Mich.

[73] Assignee: The Dow Chemical Company, Midland, Mich.

[21] Appl. No.: 284,034

[22] Filed: Jul. 17, 1981

[51] Int. Cl.$^3$ .............................................. C07F 7/18
[52] U.S. Cl. ................................. 204/158 R; 556/470
[58] Field of Search ...................... 556/470; 204/158 R

[56] References Cited

U.S. PATENT DOCUMENTS

| | | | |
|---|---|---|---|
| 3,069,451 | 12/1962 | Fritz ................................. | 260/448.2 |
| 3,450,737 | 6/1969 | Colleuille ......................... | 260/448.2 |
| 3,472,888 | 10/1969 | Bazouin et al. .................. | 260/448.2 |
| 3,536,745 | 10/1970 | Dear .................................. | 556/470 |
| 3,642,596 | 2/1972 | Takamizawa et al. ............ | 204/158 |
| 3,846,463 | 11/1974 | Nagai et al. ...................... | 260/448.8 |
| 3,856,843 | 12/1974 | Nagai et al. .................. | 260/448.8 R |
| 3,976,596 | 8/1976 | Hawthorne et al. ............ | 252/431 P |
| 4,127,506 | 11/1978 | Gray et al. ...................... | 252/431 N |
| 4,228,035 | 10/1980 | Gray et al. ...................... | 252/431 R |

FOREIGN PATENT DOCUMENTS 1248050 8/1967 Fed. Rep. of Germany ...... 556/470
1044448 9/1966 United Kingdom ................ 556/470

OTHER PUBLICATIONS

Jetz G. Graham, Silicon–Transition Metal Chemistry I. Photochemical Preparation of Silyl (Transition Metal) Hydrides, 10 Inorganic Chemistry 4 (1971).
Pittman, Jr., "Photocatalysis of Hydrosilylation Using Metal Carbonyls," (Abstract of talk given at the 181st ACS National Meeting held in Atlanta, GA, Mar. 29–Apr. 3 (1981).

*Primary Examiner*—Paul F. Shaver
*Attorney, Agent, or Firm*—Cedric M. Richeson

[57] ABSTRACT

A process to form silyl ethers by contacting a carbonyl compound with an organosilicon hydride under reaction conditions in the presence of a catalyst, said catalyst being formed from a transition metal carbonyl coordination compound precursor by irradiation at an appropriate wavelength.

25 Claims, 2 Drawing Figures

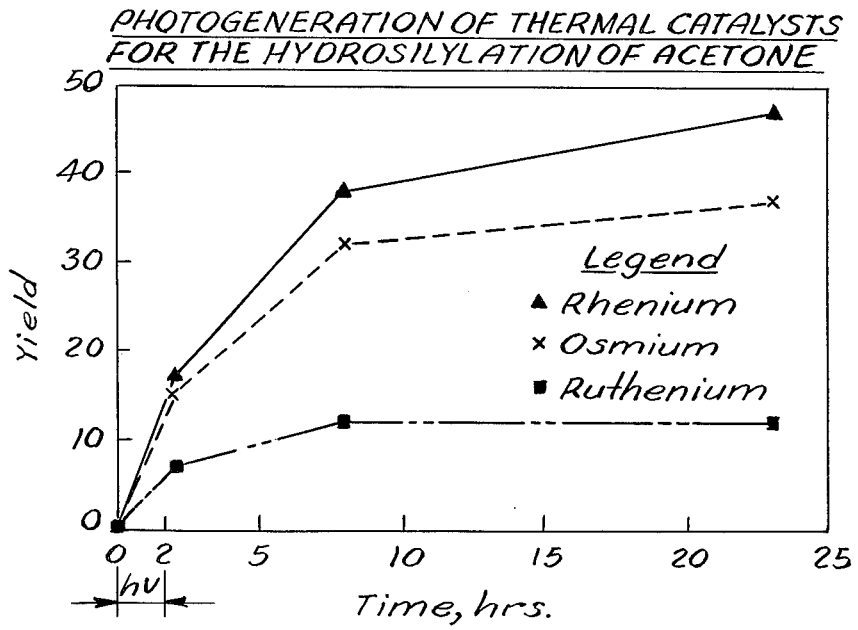
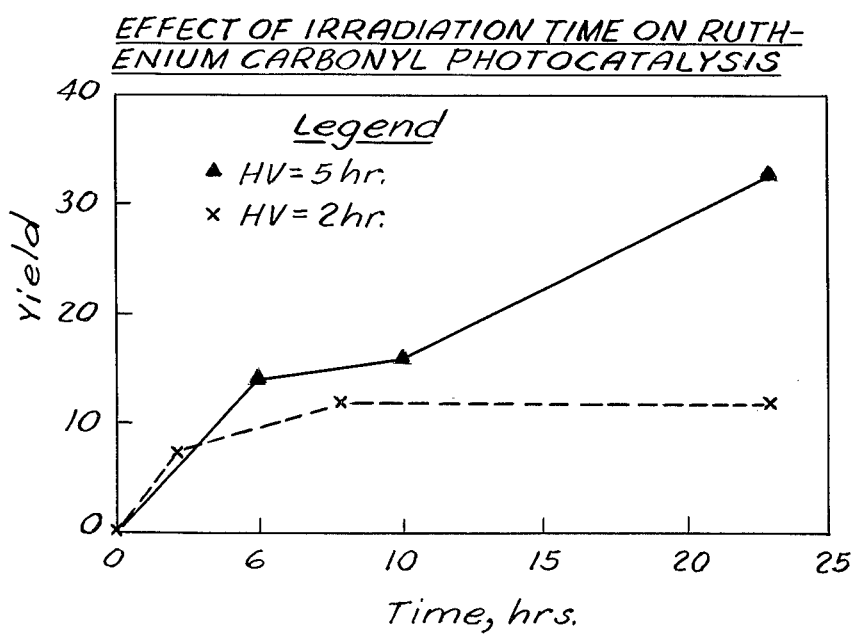

PHOTOACTIVATED CATALYTIC HYDROSILYLATION OF CARBONYL COMPOUNDS

BACKGROUND OF THE INVENTION

This invention relates to an improved catalytic process for preparing silyl ethers. In particular, the invention relates to a process for preparing silyl ethers by photoactivated catalysis of carbonyl compounds with organosilicon hydrides generally under mild conditions.

It is known to produce silyl ethers by reacting carbonyl compounds with organosilicon hydrides in the presence of catalysts. Such a process which utilizes a phosphine halo-rhodium catalyst is disclosed in U.S. Pat. No. 3,856,843. There, suitable carbonyl compounds such as aldehydes and ketones are shown as well as suitable organosilicon hydrides. Preparation of vinyloxy-containing organosilicon compounds using zinc-chloride as a catalyst are shown in U.S. Pat. No. 3,472,888. Reaction of acetone with silane at high temperatures (300° C.–600° C.) is described in U.S. Pat. No. 3,069,451. This patent also discloses that ultraviolet light may be used to catalyze the reaction.

SUMMARY OF THE INVENTION

According to the present invention, the process comprising contacting a carbonyl compound with an organosilicon hydride under reaction conditions to form a silyl ether is improved by utilizing at least one of several catalysts. The process of the instant invention incorporates a transition metal carbonyl coordination compound precursor. This precursor upon exposure to electromagnetic radiation decomposes to a plurality of species including at least one species hereinafter termed "photoactivated" that is catalytically active with respect to the above reaction. Therefore, the reaction can be controlled by the presence or absence of radiation to produce a catalytic amount of photoactivated species. Subsequent to irradiation, the reaction will proceed even after removal of the radiation source. How long the reaction proceeds after this removal generally depends on the length of exposure to radiation as well as the particular catalyst precursor. Elevated temperatures are unnecessary to promote this reaction. Therefore, in one aspect, this invention provides a process which allows flexibility in operation as to process reaction conditions and catalyst choice.

BRIEF DESCRIPTION OF THE DRAWINGS

FIG. 1 is a graph comparing three catalysts in the process of the invention. Yield is plotted against continuous time with an initial period of irradiation.

FIG. 2 is a graphic comparison of a ruthenium catalytic process utilizing varying periods of initial irradiation.

DETAILED DESCRIPTION OF THE INVENTION

The invention employs as a reactant a carbonyl compound or mixtures thereof. Any carbonyl compound which has a utilizable radiation absorption band which does not substantially overlap that of the catalyst should be suitable. While the instant invention can be carried out with some overlap, it is critical that the catalyst precursor absorb enough radiation to produce the catalytically active species in sufficient quantity to promote the reaction. If the absorption bands of the catalyst and a reactant overlap, then the possibility exists that the reactant will absorb enough radiation to inhibit the formation of the desired catalytically active species. This possibility is greatly enhanced by the relatively large concentration of reactant compared to the concentration of catalyst precursor. Therefore, no overlap is to be preferred while some overlap is tolerable. Suitable carbonyl compounds include ketones, esters and aldehydes with or without side chains or substituents. A few common examples are aliphatic ketones or aldehydes, aromatic ketones or aldehydes, and terpene ketones or aldehydes. Preferred examples are acetone, 2-heptanone, cycloheptanone, n-butyraldehyde and acetophenone.

The invention also employs as a reactant an organosilicon hydride. Necessary is an organosilicon hydride having at least one active Si—H group. Therefore, disilicon compounds are encompassed by the invention. Suitable organosilicon hydrides include those of the formula $H_xSiR_y$ wherein R is hydrocarbyl such as alkyl, aryl, arylalkyl, alkylaryl, and either straight-chained, branch-chained or cyclo or combinations thereof; and $x=1$ or 2; $y=2$ or 3 and $x+y=4$. Examples of these suitable compounds include trialkylsilanes such as triethylsilane, diethylmethylsilane and tributylsilane; dialkylsilanes; diarylalkylsilanes; diarylsilanes; arylalkylsilanes; alkylarylsilanes and arylsilanes. Preferred alkyl groups are the lower alkyl groups having 1–7 carbon atoms. The preferred aryl group is phenyl. Examples of preferred organosilicon hydrides are triethylsilane, diethylsilane, dimethylphenylsilane and diethylmethylsilane.

Suitable catalyst precursors for the process of this invention are transition metal carbonyl coordination compounds. Preferred are tetrairidium dodecacarbonyl $[Ir_4(CO)_{12}]$, dirhenium decacarbonyl $[Re_2(CO)_{10}]$, tetracobalt dodecacarbonyl $[Co_4(CO)_{12}]$, triphenylphosphine cobalt tricarbonyl dimer $[Co_2(CO)_6(PPh_3)_2]$, dicarbonyl acetylacetonato iridium $[Ir(CO)_2(C_5H_7O_2)]$, triosmium dodecacarbonyl $[Os_3(CO)_{12}]$, triruthenium dodecacarbonyl $[Ru_3(CO)_{12})]$, hexarhodium hexadecacarbonyl $[Rh_6(CO)_{16})]$, chromium hexacarbonyl $[Cr(CO)_6]$ and dicobalt octacarbonyl $[Co_2(CO)_8]$.

A catalytic amount of photoactivated species of a transition metal carbonyl coordination compound precursor is required for the practice of this invention. This necessitates the inclusion of a sufficient amount of the precursor to allow formation of the required activated species. Typically, the catalyst precursor is present at a minimum precursor:reactants weight ratio of about 1:1000 and preferably of about 1:700. These ratios are typical with the actual ratios determined by the specific catalysts and reactants used as well as practical considerations such as convenience and economy.

Any radiation source is suitable which produces a catalyst comprising at least one photoactivated species of a transition metal carbonyl coordination compound precursor. The preferred electromagnetic radiation is that having wavelengths within a range from about 200 nanometers to about 850 nanometers (hereinafter termed "ultraviolet" range) (Note this range as defined here is broader than the typical UV range and encompasses the visible range and beyond up to about 850 nanometers). It is not necessary that the radiation source cover the entire range, only that some radiation be emitted that has a wavelength falling within this range. The wavelength of choice may vary depending upon the particular reactants and catalyst precursor used in the reaction. Examples of devices comprising suitable radiation sources include low, medium or high pressure mercurcy arc lamps and monochromatic lasers.

Without wishing to be bound by any specific theory, it is believed that coordinatively unsaturated metal complexes are the reactive species which catalyze the process reaction. Coordinatively unsaturated metal complexes are considered molecular fragments of organometallic complexes. These fragments are conveniently produced by irradiation of the complexes. A well-known example of this production is:

$$Cr(CO)_6 \xrightarrow{h\nu} [Cr(CO)_5] + CO. \qquad I$$

Here a coordinatively unsaturated species, viz. $[Cr(CO)_5]$, is produced by the photoinduced expulsion of a labile ligand, viz. CO. Note however, that it is possible that suitable coordinatively unsaturated species are produced by mechanisms other than ligand expulsion, e.g., metal-metal bond cleavage. These coordinatively unsaturated complexes are extremely reactive and undergo further reactions. For example, $Fe(CO)_4$ which can be photogenerated from $Fe(CO)_5$ reacts readily with $HSiEt_3$ to form a silane complex:

$$Fe(CO)_5 \xrightarrow[HSiEt_3]{h\nu} Fe(CO)_4(H)(SiEt_3) + CO. \qquad II$$

The reaction in I with subsequent expulsion of additional labile ligands may be generalized by the following reactions wherein hv=ultraviolet radiation, M=transition metal, L=ligand and X is a positive integer.

$$ML_x \underset{}{\overset{h\nu}{\rightleftarrows}} ML_{x-1} + L \qquad III$$

$$ML_{x-1} \longrightarrow ML_{x-2} + L \qquad IV$$

$$ML_{x-n+1} \longrightarrow ML_{x-n} + L \qquad V$$

Reaction III is photoinitiated; however, reactions IV-V can either be photoinitiated or thermally initiated. In either case, the species produced $ML_{x-2}$-$ML_{x-n}$ result from an initial absorption of radiation by $ML_x$. In the instant invention, the catalytically active species may be formed in the primary step III or may result from either photo or thermal decomposition of an unstable intermediate to an eventual catalyst $ML_{x-n}$ in subsequent steps. If a thermal catalyst is being formed via step III or subsequent decomposition steps, its activity should continue after the initial period of irradiation stops. Table I contains data showing this continued activity.

TABLE I

Photogeneration of Thermal Catalysts for Hydrosilylation of Acetone

| # | Catalyst Precursor (CP) | Time (hr) A[1] | Time (hr) B[2] | Reactants (moles) Acetone | Reactants (moles) HSiEt3 | CP (moles) | Yield[3] |
|---|---|---|---|---|---|---|---|
| 1 | Re2(CO)10 | 2 | 0 | 0.0045 | 0.0041 | 3 × 10⁻⁶ | 17 |
| 2 | " | 5 | 0 | " | " | " | 100[4] |
| 3 | " | 2 | 6 | " | " | " | 38 |
| 4 | " | 2 | 21 | " | " | " | 47 |
| 5 | Ru3(CO)12 | 0 | 22 | " | " | " | 1 |
| 6 | " | 2 | 0 | " | " | " | 7 |
| 7 | " | 2 | 6 | " | " | " | 12 |
| 8 | " | 2 | 21 | " | " | " | 12 |
| 9 | " | 5 | 0 | " | " | " | 14 |
| 10 | " | 5 | 5 | " | " | " | 16 |
| 11 | " | 5 | 17 | " | " | " | 33 |
| 12 | Os3(CO)12 | 2 | 0 | " | " | " | 15 |
| 13 | " | 2 | 6 | " | " | " | 32 |
| 14 | " | 2 | 21 | " | " | " | 37 |

[1] hv at 29° C.
[2] No hv at ambient temperature.
[3] % Yield $(CH_3)_2CHOSiEt_3$ based on quantitative gas chromatographic analysis using a toluene internal standard.
[4] Yield for Run 2 is actually conversion of $HSiEt_3$ and not quantitative product yield. Experience has shown that roughly 15 percent of the figure for conversion is by-product.

The data in Table I was obtained using the apparatus and procedure of Example 1 described hereinafter. However, in runs 3–5, 7, 8, 10, 11, 13 and 14, the reaction mixture was allowed to stand for the indicated time. The percentage yields were determined by quantitative gas chromatographic analysis using a toluene internal standard. Comparison of the runs in which the reaction was allowed to proceed at ambient temperature in darkness after 2 hours of irradiation at 350 nanometers at 29° C., reveals that the catalytic precursor $Re_2(CO)_{10}$ yielded the most product. The three catalysts are graphically compared in FIG. 1. Since $Os_3(CO)_{12}$ and $Ru_3(CO)_{12}$ have similar quantum yields of disappearance (see Wrighton et al., 168 Advances in Chemistry Series, p. 207 (1978) published by the American Chemical Society, Vol. 168 is entitled "Inorganic and Organometallic Photochemistry"), then it follows that the osmium catalyst is more active than the ruthenium catalyst toward the hydrosilylation of acetone.

However, it is to be noted that the amount of dark reaction can be dependent upon the duration of the initial radiation as seen by comparing runs 5–11 of Table I. This data is compared graphically in FIG. 2 for ruthenium carbonyl.

One or more of the photoactivated species of a catalyst precursor formed from primary or secondary steps III through V will exhibit thermal catalytic behavior. Also, one photon can produce a catalyst which will react many substrate molecules before deactivating. The quantum yields resulting from irradiation of the three catalyst precursors of Table I are shown in Table II. These yields are given as the moles product:moles photons ratio Φ.

TABLE II

Quantum Yields of Product Formation for the Photocatalytic Hydrosilylation of Acetone

| # | Catalyst Precursor | λ (nm) | I $\frac{einsteins}{minute}$ | Φ |
|---|---|---|---|---|
| 1 | Re2(CO)10 | 365 | 1.98 × 10⁻⁶ | 6.1 |
| 2 | Ru3(CO)12 | " | " | 1.1 |
| 3 | Os3(CO)12 | " | " | 3.3 |

The quantum yield experiment yielding Table II was conducted using the same type of reaction vessel, reactants, and the same degassing and drying steps as in Example 1, infra. The reaction vessels were placed in a turntable photoreactor equipped with a 450-watt medium pressure Hanovia ® mercury arc lamp. The lamp was jacketed by a water-cooled quartz immersion well and the 365 nanometer wavelength was isolated using Corning Glass ® CS7-60 and CS0-52 filters. The experiment was conducted at ambient temperatures and the intensity (I) of the incident light upon the reaction mixture for this particular setup was $1.98 \times 10^{-6}$ einsteins per minute. Since the data of Table II reflects reaction conditions inside sealed tubes, the back reaction of the $ML_{x-n}$ species with $CO_n$ to reform the catalyst precursor was not prevented. Therefore, the quantum yields presented in Table II should be considered lower limits which may be improved by process refinement. It is important to note that not only is this reaction catalytic with respect to the activated species of the catalyst precursor, but it is also catalytic with respect to photons since $\Phi$ is greater than unity.

From the table, the order of catalytic activity is $Re_2(CO)_{10} > Os_3(CO)_{12} > Ru_3(CO)_{12}$. Interestingly, this shows that for acetone, the quantum yield for the osmium carbonyl is greater than the quantum yield for the ruthenium carbonyl. The reverse order is found in the photohydrosilylation of olefins.

It is to be noted that the process of the invention may be advantageously carried out in batch, semi-batch or continuous reactors.

The temperature at which the reaction is carried out may vary from below to above ambient temperatures with temperatures from 0° C. to 50° C. common. Ambient temperatures are preferred.

The reaction may also proceed under elevated or depressed as well as atmospheric pressures. However, it is to be noted that the reaction should not be carried out in an open vessel since the reaction mixture will generally have been degassed to remove dissolved oxygen which poisons the catalyst. In some cases excess carbon monoxide may also act to deactivate the catalyst and should be avoided. Degassing may be accomplished in various ways known to those skilled in the art. Two common methods are purging with nitrogen or subjecting the reaction vessel and its contents to repetitive freeze-pump-thaw cycles. Utilizing either method will allow the reaction to be carried out in an inert environment thereby preserving the catalyst and avoiding unwanted side reactions.

Reaction times from about 1 to about 10 hours are expected with a reaction time of 1-5 hours being preferred. Reaction time will generally be based upon practical considerations such as convenience, economy, catalyst choice as well as the particular reactants used.

Normally, substantially equivalent amounts of the organosilicon hydride are reacted with the carbonyl compound. However, the amounts of both reactants can be altered depending upon the degree of hydrosilylation desired.

The process of the invention can produce high yields of silyl ether products. However, care should be used to avoid the presence of water in the reaction as $H_2O$ competes with carbonyl compounds via side reactions with the organosilicon hydride reactants. For example,

$$HSiEt_3 \xrightarrow{H_2O} Et_3Si-O-SiEt_3.$$

The silyl ethers produced by the process of this invention have well-known utilities including use in industry in water-proofing agents, silicon lacquers, polymer transparency improving agents, siloxane polymer plasticizers and in the preparation of silicon resins. Moreover, silyl ethers are thermally stable and easily analyzed by conventional analytical techniques. Therefore, this invention may be employed to protect or analyze compounds containing an active hydrogen atom by the intermediate formation of organosilyl protected compounds. Since the instant invention allows the reaction to occur under mild conditions, this process can be an important new method for reducing sensitive carbonyl molecules, e.g., to alcohols via hydrolysis of an intermediate silyl ether, especially in the synthesis of fine chemicals such as pharmaceuticals or agricultural chemicals.

Following are examples given to illustrate the process of the invention, but these examples should not be taken as limiting the scope. For example, all of the examples presented below represent homogeneous catalysis, but the preparation of a supported catalyst is possible, see e.g., U.S. Pat. Nos. 4,127,506 and 4,228,035 which disclose polymer supported photoactivated catalysts useful in the hydroformylation of olefins and hydrogenation of olefins, respectively.

Unless otherwise specified, the following reactions were all conducted utilizing as the reaction vessel, a Pyrex ® tube equipped with a high vacuum stop-cock and Teflon ® plug. Irradiation occurred after placing the vessel in a Rayonet ® photoreactor equipped with RPR ® 3500 A lamps whose spectral output is a maximum at 350 nanometers. The operating temperature of the photoreactor was measured at 29° C. The carbonyl compounds and organosilicon hydrides were all distilled and kept dry over molecular sieve absorbents.

EXAMPLE 1

Photohydrosilylation of Acetone

A reaction vessel was charged with 0.791 grams (1 ml, 0.014 mole) of acetone, 1.46 grams (2 ml, 0.012 mole) of triethyl silicon hydride [$HSi(CH_2CH_3)_3$], and ($3 \times 10^{-6}$ mole) of catalyst precursor. The reaction mixture was thoroughly degassed by four freeze-pump-thaw cycles. After degassing, the reaction mixture was irradiated for 20 hours and the contents analyzed by standard vapor phase chromatographic techniques. The results are shown in Table III. Runs 6, 10, 11, 12 and 13 of Table III were similarly performed but using 0.261 grams (0.33 ml, 0.0045 mole) of acetone, 0.47 grams (0.66 ml, 0.0041 mole) of triethyl silicon hydride and $1 \times 10^{-6}$ mole of catalyst precursor.

TABLE III

| # | Catalyst Precursor | Photoactivated Catalyzed Hydrosilylation of Acetone | |
|---|---|---|---|
| | | % Yield Silyl ether[1] | % $HSiEt_3$ Conversion[2] |
| 1 | None | ND[3] | 17 |
| 2 | $Re_2(CO)_{10}$ | 87 | 100 |
| 3 | $Ir_4(CO)_{12}$ | 86 | 100 |
| 4 | $Os_3(CO)_{12}$ | 83 | 100 |
| 5 | $Ru_3(CO)_{12}$ | 87 | 100 |
| 6 | $Ir(CO)_2(C_5H_7O_2)$ | ND | 100 |
| 7 | $Fe_3(CO)_{12}$ | 5 | 11 |

TABLE III-continued

| | | Photoactivated Catalyzed Hydrosilylation of Acetone | |
|---|---|---|---|
| # | Catalyst Precursor | % Yield Silyl ether[1] | % HSiEt$_3$ Conversion[2] |
| 8 | Co$_2$(CO)$_8$ | 25 | 37 |
| 9 | Cr(CO)$_6$ | 25 | 41 |
| 10 | Rh$_6$(CO)$_{16}$ | ND[3] | 77 |
| 11 | Co$_2$(CO)$_6$(PPh$_3$)$_2$ | ND | 6 |
| 12 | Co$_4$(CO)$_{12}$ | ND | 47 |
| 13 | Fe$_2$(CO)$_9$ | ND | 10 |

[1] The main product is triethylisopropoxysilane (C$_9$H$_{22}$OSi) with the quantitative yield determined by vapor phase chromatography using a toluene internal standard.
[2] The conversion gives a relative yield of product with the difference between [1] and [2] being largely Et$_3$Si—O—SiEt$_3$ due to the presence of water in the run.
[3] Not determined.

In Example 1, the silyl ether product was identified by proton nuclear magnetic resonance (NMR), elemental analysis and gas chromatographic mass spectrometry analysis to be the following hydrosilylation adduct of acetone given in the reaction:

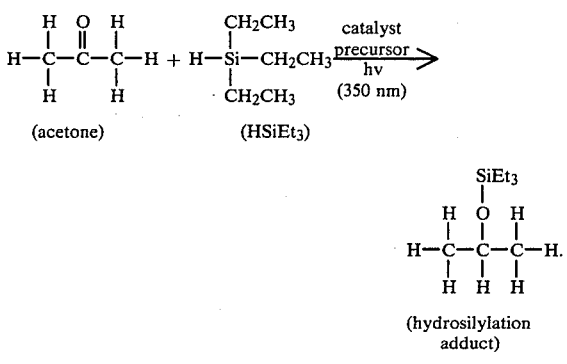

While the photocatalyzed hydrosilylation of olefins results in a multitude of products, e.g.:

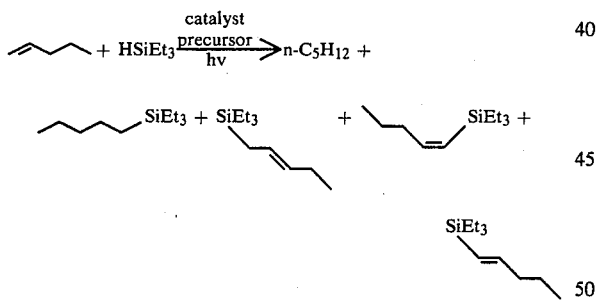

the photocatalyzed hydrosilylation of acetone was selective to a single product. Also, as can be seen from Table III, the most effective catalyst precursors were the carbonyl compounds of Ir, Os, Ru, Re and Rh. Interestingly, Fe$_3$(CO)$_{12}$, Fe$_2$(CO)$_9$, Co$_2$(CO)$_8$ and Co$_4$(CO)$_{12}$ which are known to be effective photoactivated catalyst precursors for the hydrosilylation of olefins were found to be relatively poor choices for the photohydrosilylation of acetone.

Run #1 of Example 1 is a comparison run not of this invention which shows that when acetone and HSiEt$_3$ were photolyzed in the Rayonet reactor in the absence of a catalyst precursor for 20 hours, about 17 percent conversion of HSiEt$_3$ occurred. This conversion presumably arose via the n$\pi$* triplet state of acetone. Ultraviolet spectroscopy shows, however, that the catalyst precursor absorbs initially greater than about 98 percent of the incident light thereby making this reaction pathway a minor contributor to product formation. When this experimental run was repeated utilizing a filtered mercury lamp to give a wavelength of 365±20 nanometers, no product was detected. Acetone does not absorb radiation at this wavelength region relative to the 350±20 nanometer region utilized in Run #1.

EXAMPLE 2

(Comparative Example) Catalytic Hydrosilylation of Acetone in Absence of Light

Example 1 was repeated with the catalyst precursors of those reactions exhibiting high activity. This time however, the reactions were allowed to proceed in the absence of light for 20 hours at 29° C. and at 80° C. The reaction vessels were charged with 0.26 grams (0.33 ml, 0.0045 mole) acetone, 0.48 grams (0.66 ml, 0.0041 mole) HSiEt$_3$ and (3×10$^{-6}$ mole) of catalyst precursor. An oil immersion bath was used to heat the reaction vessels. The results are contained in Table IV.

TABLE IV

| | Catalytic Hydrosilylation of Acetone in the Absence of Light | | |
|---|---|---|---|
| # | Catalyst Precursor | Temp. °C. | Time (hr) | % HSiEt$_3$ Conversion |
| 1 | Ir$_4$(CO)$_{12}$ | 29 | 20 | <1 |
| 2 | Re$_2$(CO)$_{10}$ | 29 | 20 | <1 |
| 3 | Ru$_3$(CO)$_{12}$ | 29 | 20 | <1 |
| 4 | Os$_3$(CO)$_{12}$ | 29 | 20 | <1 |
| 5 | Co$_4$(CO)$_{12}$ | 29 | 20 | <1 |
| 6 | Fe$_3$(CO)$_{12}$ | 29 | 20 | <1 |
| 7 | Ir$_4$(CO)$_{12}$ | 80 | 20 | 6 |
| 8 | Re$_2$(CO)$_{10}$ | 80 | 20 | 10 |
| 9 | Ru$_3$(CO)$_{12}$ | 80 | 20 | 100 |
| 10 | Os$_3$(CO)$_{12}$ | 80 | 20 | 76 |
| 11 | Co$_4$(CO)$_{12}$ | 80 | 20 | 3 |
| 12 | Fe$_3$(CO)$_{12}$ | 80 | 20 | 34 |

Comparison of Example 1 with Example 2 shows that only a small amount of reaction occurred in the dark at 29° C. which was the operating temperature of the reactor used. Light therefore is a crucial component of the catalytic reaction; with the activation of the catalyst precursors due to irradiation. Note that in some instances heat will bring about increased conversion (Runs 9 and 10 of Table IV) in the absence of irradiation.

EXAMPLE 3

Photohydrosilylation of 2-Heptanone

A reaction vessel was charged with 1.23 grams (1.5 ml, 0.011 mole) of 2-heptanone, 1.095 grams (1.5 ml, 0.009 mole) of triethylsilicon hydride (HSiEt$_3$), and (3×10$^{-6}$ mole) of catalyst precursor. The reaction mixture was then degassed as in the above examples and irradiated for 20 hours. The contents were analyzed using vapor phase chromatography. The results are shown in Table V.

TABLE V

| | Photoactivated Catalyzed Hydrosilylation of 2-Heptanone | | |
|---|---|---|---|
| # | Catalyst Precursor | Temp. °C. | Time (hr) | % HSiEt$_3$ Conversion |
| 1 | Ir$_4$(CO)$_{12}$ | 29 | 20 | 93 |
| 2 | Re$_2$(CO)$_{10}$ | 29 | 20 | 95 |
| 3 | Ru$_3$(CO)$_{12}$ | 29 | 20 | 21 |
| 4 | Os$_3$(CO)$_{12}$ | 29 | 20 | 28 |

TABLE V-continued

Photoactivated Catalyzed Hydrosilylation of 2-Heptanone

| # | Catalyst Precursor | Temp. °C. | Time (hr) | % HSiEt$_3$ Conversion |
|---|---|---|---|---|
| 5 | Fe$_3$(CO)$_{12}$ | 29 | 20 | 0 |

The results of Example 3 demonstrate that the catalytic hydrosilylation of ketones is very dependent upon the catalyst. For example, Os$_3$(CO)$_{12}$ is an effective photocatalyst precursor for acetone but a relatively poor one for 2-heptanone. Since Run 5 produces no silyl ether it is not an example of the invention. The significance of Table V lies in its showing that catalyst precursors will vary depending upon the reactants chosen and that the process of the invention requires that both reactants and catalyst precursor be chosen so as to produce a silyl ether product. A conversion of greater than 50 percent is to be preferred.

EXAMPLE 4

Photohydrosilylation of Acetone and Reduction to 2-Propanol

A reaction vessel was charged with 1.16 grams (1.5 ml, 0.02 mole) of acetone, 1.09 grams (1.5 ml, 0.01 mole) of triethylsilicon hydride (HSiEt$_3$) and 0.0031 grams ($5 \times 10^{-6}$ mole) Re$_2$(CO)$_{10}$. After degassing and irradiation as described in the above examples, the reaction mixture containing the silyl ether product was hydrolyzed by addition of 10 ml of methanol containing 0.1 percent p-toluene sulfonic acid at 0° C. After standing overnight, a vapor phase chromatographic analysis showed quantitative conversion of the silyl ether to 2-propanol. Example 4 demonstrates utility as a new method for reducing carbonyl molecules to alcohols.

EXAMPLE 5

Photohydrosilylation of Cycloheptanone

A reaction vessel was charged with 1.23 grams (1.3 ml, 0.011 mole) of cycloheptanone, 1.2 grams (1.6 ml, 0.01 mole) of triethylsilicon hydride (HSiEt$_3$) and 0.0037 grams ($3.3 \times 10^{-6}$ mole) Ir$_4$(CO)$_{12}$. The reaction mixture was then degassed and irradiated as described in the above examples. A vapor phase chromatographic analysis revealed an 18 percent conversion to one major product. Further analysis by a gas chromatographic mass spectrometer apparatus showed this product to be the hydrosilylation adduct.

EXAMPLE 6

Photohydrosilylation of n-Butyraldehyde

A reaction vessel was charged with 0.94 grams (1.1 ml, 0.013 mole) of freshly distilled n-butyraldehyde, 1.39 grams (1.9 ml, 0.012 mole) of triethylsilicon hydride and ($3 \times 10^{-6}$ mole) of catalyst precursor. The reaction mixture was degassed and irradiated as described in the above examples. The results are shown in Table VI.

TABLE VI

Photoactivated Catalyzed Hydrosilylation of n-Butyraldehyde

| # | Catalyst Precursor | Temp. °C. | Time (hr) | % HSiEt$_3$ Conversion |
|---|---|---|---|---|
| 1 | Ir$_4$(CO)$_{12}$ | 29 | 20 | 7 |
| 2 | Re$_2$(CO)$_{10}$ | 29 | 20 | 53 |

TABLE VI-continued

Photoactivated Catalyzed Hydrosilylation of n-Butyraldehyde

| # | Catalyst Precursor | Temp. °C. | Time (hr) | % HSiEt$_3$ Conversion |
|---|---|---|---|---|
| 3 | Co$_4$(CO)$_{12}$ | 29 | 20 | 100 |
| 4 | Fe$_3$(CO)$_{12}$ | 29 | 20 | 8 |
| 5 | Cr(CO)$_6$ | 29 | 20 | 9 |
| 6 | Co$_2$(CO)$_6$(PPh$_3$)$_2$ | 29 | 20 | 100 |

Example 6 shows that two poor catalyst precursors for acetone (see Table III, Runs 17 and 18) are good ones for n-butyraldehyde. Also Ir$_4$(CO)$_{12}$ which worked well for acetone worked poorly for n-butyraldehyde. Therefore the optimum choice of catalyst precursor may be readily determined experimentally.

EXAMPLE 7

Selective Hydrosilylation of Aldehydes

A reaction vessel was charged with 0.38 grams (0.48 ml, 0.0065 mole) of acetone, 0.47 grams (0.57 ml, 0.0065 mole) of n-butyraldehyde, 1.39 grams (1.9 ml, 0.012 mole) of triethylsilicon hydride and ($5 \times 10^{-6}$ mole) of catalyst precursor. The reaction mixture was degassed and irradiated as described in the above examples. Analysis by vapor phase chromatography revealed that the butyraldehyde was quantitatively converted to the silyl ether while only a small amount of acetone was consumed. The normalized results are given in Table VII.

TABLE VII

Selective Hydrosilylation of Aldehydes

| | | | | Product Mixture in Percentage | | |
|---|---|---|---|---|---|---|
| # | Catalyst Precursor | Acetone | n-Butyraldehyde | HSiEt$_3$ | OSiEt$_3$ (iPr) | OSiEt$_3$ (n-Bu) |
| 1 | Ir$_4$(CO)$_{12}$ | 23 | 10 | 63 | 2 | 2 |
| 2 | Co$_4$(CO)$_{12}$ | 22 | 0 | 22 | 4 | 52 |

Example 7 expands upon the teaching of Example 6 to demonstrate that mixtures of ketones and aldehydes may be selectively converted to silyl ether products.

As mentioned before, the above examples serve only to illustrate the invention and its advantages, and they should not be interpreted as limiting since further modifications of the disclosed invention will be apparent to those skilled in the art. All such modifications are deemed to be within the scope of the invention as defined by the following claims.

What is claimed is:

1. A process comprising contacting a carbonyl compound with an organosilicon hydride under reaction conditions to form a silyl ether in the presence of a catalytic amount of at least one photoactivated species of a transition metal carbonyl coordination compound precursor.

2. A process as defined in claim 1 wherein said photoactivated species are formed by irradiating said precursor with electromagnetic radiation comprising a plurality of wavelengths from a range of about 200 nanometers to about 850 nanometers.

3. A process as defined in claim 2 wherein said precursor is tetrairidium dodecacarbonyl.

4. A process as defined in claim 2 wherein said precursor is dirhenium decacarbonyl.

5. A process as defined in claim 2 wherein said precursor is tetracobalt dodecacarbonyl.

6. A process as defined in claim 2 wherein said precursor is triphenylphosphine cobalt tricarbonyl dimer.

7. A process as defined in claim 2 wherein said precursor is dicarbonylacetylacetonato iridium.

8. A process as defined in claim 2 wherein said precursor is triosmium dodecacarbonyl or triruthenium dodecacarbonyl.

9. A process as defined in claim 2 wherein said precursor is hexarhodium hexadecacarbonyl, chromium hexacarbonyl or dicobalt octacarbonyl.

10. A process as defined in claim 2 wherein said reaction conditions include a reaction environment that is substantially free of reaction inhibiting oxygen or water.

11. A process as defined in claim 2 wherein said carbonyl compound is a ketone.

12. A process as defined in claim 2 wherein said carbonyl compound is acetone.

13. A process as defined in claim 11 wherein said precursor is tetrairidium dodecacarbonyl, dirhenium decacarbonyl, tetracobalt dodecacarbonyl, triphenylphosphine cobalt tricarbonyl dimer, dicarbonylacetylacetonato iridium, triosmium dodecacarbonyl, triruthenium dodecacarbonyl, hexarhodium hexadecacarbonyl, chromium hexacarbonyl or dicobalt octacarbonyl.

14. A process as defined in claim 2 wherein said carbonyl compound is an aldehyde.

15. A process as defined in claim 14 wherein said precursor is dirhenium decacarbonyl, tetracobalt dodecacarbonyl or triphenylphosphine cobalt tricarbonyl dimer.

16. A process as defined in claim 15 wherein said aldehyde is n-butyraldehyde.

17. A process as defined in claim 11 wherein said precursor is tetrairidium dodecacarbonyl, dirhenium decacarbonyl, dicarbonylacetylacetonato iridium, triosmium dodecacarbonyl or triruthenium dodecacarbonyl.

18. A process as defined in claim 17 wherein said ketone is acetone.

19. A process as defined in claim 3 wherein said carbonyl compound is cycloheptanone.

20. A process as defined in claim 2 or 5 wherein a mixture of carbonyl compound is present.

21. A process as defined in claim 3 or 4 wherein said carbonyl compound is 2-heptanone.

22. A process as defined in claim 13, 15, 17 or 18 wherein said organosilicon hydride is of the formula $H_xSiR_y$ where R is alkyl or aryl; $x=1$ or 2; $y=2$ or 3 and $x+y=4$.

23. A process as defined in claim 22 wherein said organosilicon hydride is $HSi(CH_2CH_3)_3$.

24. A process as defined in claim 10 wherein said reaction conditions include reacting at a temperature within the range of about 0° C. to about 50° C.

25. A process as defined in claim 1 wherein the transition metal of said precursor is iridium, rhenium, cobalt, ruthenium, rhodium, chromium or osmium.

* * * * *